United States Patent [19]

Skuballa et al.

[11] Patent Number: 4,954,524
[45] Date of Patent: Sep. 4, 1990

[54] CARBACYLCINS, THEIR PREPARATION AND USE AS MEDICINAL AGENTS

[75] Inventors: Werner Skuballa; Bernd Raduechel; Helmut Vorbrueggen, all of Berlin; Jorge Casals-Stenzel, Mainz; Gerda Mannesmann, Cologne; Ekkehard Schillinger; Michael H. Town, both of Berlin, all of Fed. Rep. of Germany

[73] Assignee: Schering Aktiengesellschaft, Berlin and Bergkamen, Fed. Rep. of Germany

[21] Appl. No.: 333,812

[22] Filed: Apr. 6, 1989

Related U.S. Application Data

[63] Continuation of Ser. No. 188,944, May 2, 1988, abandoned, which is a continuation of Ser. No. 77,279, Jul. 24, 1987, abandoned, which is a continuation of Ser. No. 859,977, May 5, 1986, abandoned, which is a continuation of Ser. No. 510,121, Jul. 1, 1983, abandoned.

[30] Foreign Application Priority Data

Jul. 13, 1982 [DE] Fed. Rep. of Germany ....... 3225287

[51] Int. Cl.$^5$ .................. C07C 177/00; H61K 31/557
[52] U.S. Cl. ..................................... 514/530; 514/460; 514/473; 514/573; 514/569; 549/427; 549/501; 556/437; 558/52; 560/56; 560/110; 560/119; 560/256; 562/466; 562/498; 562/501
[58] Field of Search ................. 560/119, 56, 116, 256; 562/503, 466, 498; 514/530, 573, 460, 473, 569; 544/427, 501; 556/437; 558/52

[56] References Cited

U.S. PATENT DOCUMENTS

| | | | |
|---|---|---|---|
| 4,238,414 | 12/1980 | Morton | 560/119 |
| 4,307,711 | 12/1981 | Gandaffi | 560/119 |
| 4,349,689 | 9/1982 | Aristoff | 560/119 |
| 4,420,632 | 12/1983 | Aristoff | 560/119 |
| 4,423,067 | 12/1983 | Skubala | 562/501 |
| 4,497,830 | 9/1985 | Skuballa | 560/119 |

FOREIGN PATENT DOCUMENTS 3306123  9/1984  Fed. Rep. of Germany ...... 560/119

*Primary Examiner*—Robert Gerstl
*Attorney, Agent, or Firm*—Millen, White & Zelano

[57] ABSTRACT

Carbacyclin derivatives of Formula I

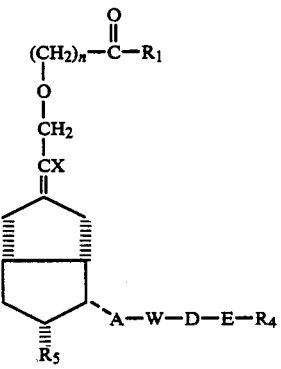

wherein
$R_1$ is hydrogen or $OR_2$, wherein $R_2$ is hydrogen, alkyl, cycloalkyl, aryl,

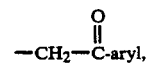

or a heterocyclic residue; or $R_1$ is $NHR_3$ wherein $R_3$ is an acid residue (acyl) or $R_2$,
n is 2, 3, 4, or 5,
X is hydrogen or fluorine,
A is —CH$_2$—CH$_2$—, trans—CH=CH—, or —C≡C—,
W is a free or functionally modified hydroxymethylene group or a free or functionally modified

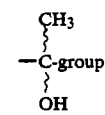

wherein the OH-group can be in the α- or β-position,
D is

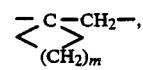

a straight-chain, saturated aliphatic group of 1–10 carbon atoms, a branched, saturated or a straight-chain or branched, unsaturated aliphatic group of 2–10 carbon atoms, all of which can optionally be substituted by fluorine atoms,
m is 1, 2, or 3,
E is a direct bond, —C≡C—, or —CR$_6$=CR$_7$— wherein $R_6$ and $R_7$ are different from each other and are hydrogen or alkyl or 1–5 carbon atoms, or are hydrogen or halogen,
$R_4$ is an aliphatic group, cycloalkyl, or optionally substituted aryl, or a heterocyclic group; and
$R_5$ is a free or functionally modified hydroxy group; and
when $R_1$ is OH, the salts thereof with physiologically compatible bases, have valuable pharmacological properties.

46 Claims, No Drawings

NOVEL CARBACYLCINS, THEIR PREPARATION AND USE AS MEDICINAL AGENTS

This application is a continuation, of application Ser. No. 188,944, filed May 2, 1988, which is a continuation of Ser. No. 077,279, filed July 24, 1987, which is a continuation of Ser. No. 859,977, filed May 5, 1986, which is a continuation of Ser. No. 510,121, filed July 1, 1983, now abandoned.

The present invention relates to novel carbacyclin derivatives, a process for their preparation and to their use as medicinal agents.

(5E)- and (5Z)-6a-carbaprostaglandin I$_2$ analogs are disclosed in German Unexamined Laid-Open Applications DOS's Nos. 2,845,770; 2,900,352 (U.S. Pat. No. 4,322,435); No. 2,902,442 (U.S. Pat. No. 4,307,112); No. 2,904,655 (U.S. Pat. No. 4,238,414); Nos. 2,909,088; 3,048,906; and 2,912,409. The nomenclature of the compounds of this invention is based on a proposal by Morton and Brokaw (J. Org. Chem. 44 : 2880 [1979]). The synthesis of these compounds yields in all cases two double-bond isomers characterized by the symbols (5E) or (5Z). The two isomers of this prototype are clarified by the following structural formula:

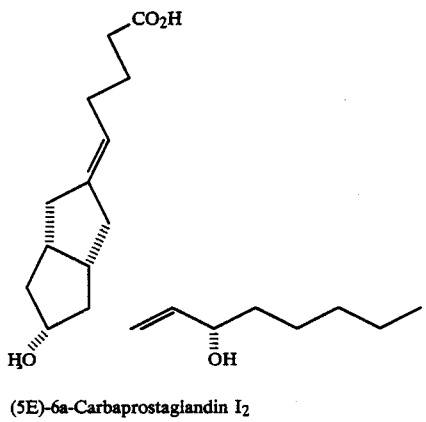

(5E)-6a-Carbaprostaglandin I$_2$

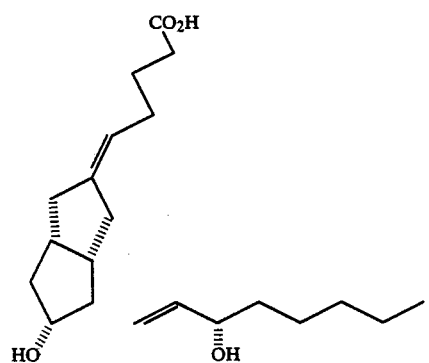

(5Z)-6a-Carbaprostaglandin I$_2$

It is known from the very voluminous state of the art of prostacyclins and their analogs that this class of compounds is suited, due to its biological and pharmacological properties, for the treatment of mammals, including man. The use of these compounds as medicinal agents, however, frequently meets with difficulties since their period of effectiveness is too short for therapeutic purposes. All structural modifications attempt to increase the duration of effectiveness as well as the selectivity of efficacy.

SUMMARY OF THE INVENTION

Accordingly, it is an object of this invention to provide new carbacyclins having such improved properties.

Upon further study of the specification and appended claims, further objects and advantages of this invention will become apparent to those skilled in the art.

These objects have been attained by providing new carbacyclin derivatives of Formula I

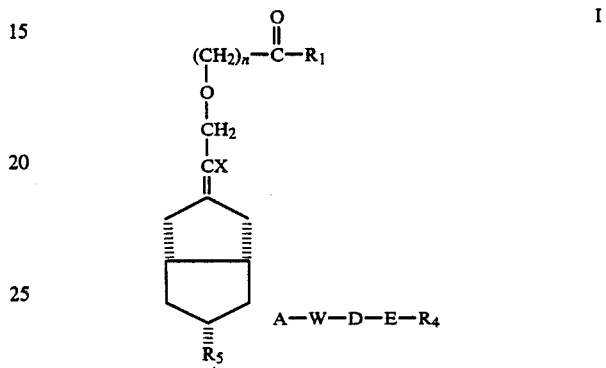

wherein
$R_1$ is hydrogen or $OR_2$, wherein $R_2$ is hydrogen, alkyl cycloalkyl, aryl,

or a heterocyclic residue; or $R_1$ is $NHR_3$ wherein $R_3$ is an acid residue (acyl) or $R_2$,
n is 2, 3, 4, or 5,
X is hydrogen or fluorine,
A is —CH$_2$—CH$_2$—, trans-CH=CH—, or —C≡C—,
W is a free or functionally modified hydroxymethylene group or a free or functionally modified

wherein the OH-group can be in the α- or β-position,
D is

a straight-chain, saturated aliphatic of 1–10 carbon atoms, a branched, saturated or a straight-chain or branched, unsaturated aliphatic group of 2–10 carbon atoms, all of which can optionally be substituted by fluorine atoms,
m is 1, 2, or 3,
E is a direct bond, —C≡C—, or —CR$_6$=CR$_7$— wherein R$_6$ is hydrogen or alkyl of 1–5 carbon atoms, and R$_7$ is hydrogen, halogen or alkyl of 1–5 carbon atoms, $R_4$ is an aliphatic group, cycloalkyl, or optionally substituted aryl, or a heterocyclic group; and $R_5$ is a free or functionally modified hydroxy group; and when $R_1$ is OH, the salts thereof with physiologically compatible bases.

It has now been found that longer duration of effectiveness, higher selectivity, and improved efficacy can be obtained in carbacyclins by homologization of the top chain of the 3-oxacarbacyclins and other variations. The compounds of this invention have blood-pressure-lowering and bronchodilatory effects. They are furthermore suitable for vasodilation, inhibition of thrombocyte aggregation and of gastric acid secretion.

DETAILED DISCUSSION

The compounds of Formula I include (5E)- as well as (5Z)-isomers.

Suitable alkyl groups $R_2$ include straight- or branched-chain alkyl groups of 1–10 carbon atoms, e.g., methyl, ethyl, propyl, isopropyl, butyl, isobutyl, tert-butyl, pentyl, isopentyl, neopentyl, heptyl, hexyl, decyl. The alkyl groups $R_2$ can optionally be mono- to polysubstituted (e.g., 2–5 substituents) by halogen atoms, hydroxy groups, $C_1$–$C_4$-alkoxy groups, optionally substituted $C_6$–$C_{10}$-aryl groups, di-$C_1$–$C_4$-alkylamines, and tri-$C_1$–$C_4$-alkylammonium. Suitable substituted aryl groups include those described below for $R_2$ per se. Monosubstituted alkyl groups are preferred. Examples of substituents include fluorine, chlorine, bromine, phenyl, dimethylamino, diethylamino, methoxy, ethoxy, etc. Preferred alkyl groups $R_2$ are those of 1–4 carbon atoms in the alkyl portion, e.g., methyl, ethyl, propyl, dimethylaminopropyl, isobutyl, butyl, etc.

Suitable aryl groups $R_2$ include substituted as well as unsubstituted aryl groups, for example phenyl, 1-naphthyl, and 2-naphthyl, each of which can be substituted by 1-3 halogen atoms, phenyl, 1-3 alkyl groups each of 1-4 carbon atoms, or a chloromethyl, fluoromethyl, trifluoromethyl, carboxy, hydroxy, or alkoxy group of 1-4 carbon atoms. Preferred is substituion in the 3- and 4-positions on the phenyl ring, for example by fluorine, chlorine, alkoxy, or trifluoromethyl, or in the 4-position by hydroxy.

Suitable cycloalkyl groups $R_2$ contain 3–10, preferably 5 or 6 carbon atoms in the ring. The rings can be substituted by alkyl groups of 1–4 carbon atoms. Examples include cyclopentyl, cyclohexyl, methylcyclohexyl, and adamantyl.

Suitable heterocyclic groups $R_2$ include 5- and 6-membered heterocycles containing at least one hetero atom, preferably nitrogen, oxygen, or sulfur, usually one such atom. The rings are normally aromatic. Examples include 2-furyl, 3-furyl, 2-thienyl, 3-thienyl, 2-pyridyl, 3-pyridyl, 4-pyridyl and others.

The aryl group in the

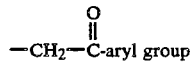

for $R_2$ can be phenyl, α- or β-naphthyl, and each can be substituted by (a) 1–3 phenyl groups, which latter, in turn, can be substituted by 1–3 halogen atoms, such as F, Cl, or Br; or by (b) 1–3 $C_1$–$C_4$-alkoxy groups or by (c) 1–3 halogen atoms (F, Cl, Br). Single substitution by phenyl, $C_1$–$C_2$-alkoxy, chlorine, or bromine is preferred.

Suitable acid residues $R_3$, i.e., acyl groups, include physiologically compatible acid residues. Preferred acids are organic carboxylic acids and sulfonic acids of 1–15 carbon atoms pertaining to the aliphatic, cycloaliphatic, aromatic, aromatic-aliphatic, and heterocyclic series. These acids can be saturated, unsaturated and/or polybasic and/or substituted in the usual way. Examples of substituents are $C_1$–$C_4$-alkyl, hydroxy, $C_1$–$C_4$-alkoxy, oxo, or amino groups, or halogen atoms (F, Cl, Br). Thus, while the acids are often hydrocarbon in nature, many diverse equivalents exist and will be readily recognized by those of skill in the art.

The following carboxylic acids are recited as examples: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di-, and trichloroacetic acids, aminoacetic acid, diethylaminoacetic acid, piperidinoacetic acid, morpholinoacetic acid, lactic acid, succinic acid, adipic acid, benzoic acid, benzoic acids substituted by halogen, trifluoromethyl, hydroxy, alkoxy, or carboxy groups, nicotinic acid, isonicotinic acid, furan-2-carboxylic acid, cyclopentylpropionic acid, etc. Especially preferred acyl residues are those of up to 10 carbon atoms. Examples of suitable sulfonic acids include methanesulfonic acid, ethanesulfonic acid, isopropanesulfonic acid, β-chloroethanesulfonic acid, butanesulfonic acid, cyclopentanesulfonic acid, cyclohexanesulfonic acid, benzenesulfonic acid, p-toluenesulfonic acid, p-chlorobenzenesulfonic acid, N,N-dimethylaminosulfonic acid, N,N-diethylaminosulfonic acid, N,N-bis(β-chloroethyl)aminosulfonic acid, N,N-diisobutylaminosulfonic acid, N,N-dibutylaminosulfonic acid, pyrrolidino-, piperidino-, piperazino-, N-methylpiperazino-, and morpholinosulfonic acids.

The hydroxy groups $R_5$ and those in W can be functionally modified, for example by etherification or esterification, wherein the free or modified hydroxy groups in W can be in the α- or β-position, free hydroxy groups being preferred.

The many suitable ether and acyl residues are well known to persons skilled in the art. Ether residues that can be easily split off are preferred, e.g., tetrahydropyranyl, tetrahydrofuranyl, α-ethoxyethyl, trimethylsilyl, dimethyl-tert-butylsilyl, and tribenzylsilyl. Suitable acyl residues include those mentioned for $R_3$. Thus, generally, these are $C_{1-15}$-hydrocarbon carboxylic and sulfonic acids and equivalents. Worth mentioning by name, for example, are acetyl, propionyl, butyryl, benzoyl, etc.

Suitable aliphatic groups $R_4$ include straight chained and branched, saturated (alkyl) and unsaturated (e.g., alkenyl) aliphatic residues, preferably alkyl groups, of 1–10, especially 1–7 carbon atoms which can optionally be substituted by optionally substituted aryl. Suitable substituents, on the latter aryl substituents, are those mentioned for the $R_2$ aryl groups per se. Examples include methyl, ethyl, propyl, butyl, isobutyl, tert-butyl, pentyl, hexyl, heptyl, octyl, butenyl, isobutenyl, propenyl, pentenyl, hexenyl, benzyl, and p-chlorobenzyl.

Cycloalkyl groups $R_4$ can contain 3–10, preferably 3–6 carbon atoms in the ring. The rings can also be substituted by alkyl groups of 1–4 carbon atoms. Examples include cyclopropyl, cyclobutyl, cyclopentyl, cyclohexyl, methylcyclohexyl, and adamantyl.

Examples of substituted and unsubstituted aryl groups $R_4$, include: phenyl, 1-naphthyl and 2-naphthyl, each of which can be substituted by 1–3 halogen atoms, phenyl, 1–3 alkyl groups of 1–4 carbon atoms each, or a chloromethyl, fluoromethyl, trifluoromethyl, carboxy, $C_1$–$C_4$-alkoxy, or hydroxy group. Substitution in the 3- and 4-positions on the phenyl ring is preferred, for example by fluorine, chlorine, $C_1$–$C_4$-alkoxy, or trifluoromethyl, or in the 4-position by hydroxy.

Suitable heterocyclic groups $R_4$ include 5- and 6-membered heterocycles containing at least one hetero atom, preferably nitrogen, oxygen, or sulfur, usually one such atom. The rings are usually aromatic. Examples include 2-furyl, 2-thienyl, 2-pyridyl, 3-pyridyl, 4-pyridyl, 3-furyl, 3-thienyl, etc.

The aliphatic groups D can be straight-chained or branched, saturated (alkylene) or unsaturated (alkenylene) residues, preferably saturated ones (alkylene) of 1–10, especially 1–5 carbon atoms which can optionally be substituted by fluorine atoms. Examples include: methylene, fluoromethylene, ethylene, 1,2-propylene, ethylethylene, trimethylene, tetramethylene, pentamethylene, 1-methyltetramethylene, 1-methyltrimethylene, etc., or also

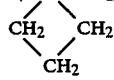

1,1-trimethylene-ethylene($-$C$-$CH$_2$), etc.

The alkyl groups $R_6$ and $R_7$ can be straightchained or branched, alkyl groups of 1–4 carbon atoms, as mentioned above for $R_2$ and $R_4$. Suitable $R_7$ halogen atoms include chlorine and bromine, preferably chlorine.

The many conventional inorganic and organic bases suitable for salt formation with the free acids ($R_1$=OH), are known to those skilled in the art for the formation of physiologically compatible salts with prostaglandin-type compounds. Examples include: alkali metal hydroxides, such as sodium and potassium hydroxide, alkaline earth metal hydroxides, such as calcium hydroxide, ammonia, amines, such as ethanolamine, diethanolamine, triethanolamine, N-methylglucamine, morpholine, tris(hydroxymethyl)methylamine, etc.

This invention furthermore relates to a process for the preparation of carbacyclin derivatives of Formula I comprising, conventionally etherifying, in the presence of a base, a compound of Formula II

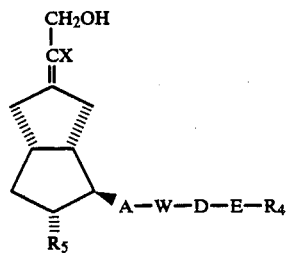

wherein X, $R_4$, $R_5$, A, W, D, and E are as defined above, optionally after blockage of any free hydroxy groups present, with a haloketal of Formula III

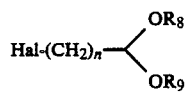

wherein
Hal is chlorine, bromine, or iodine
$R_8$ and $R_9$ each are alkyl of 1–10 carbon atoms, or $R_8$ and $R_9$ together form a group of 2–10 carbon atoms, which form with the connecting

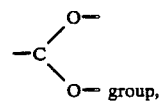

and n is as defined above,
and splitting the ketal with an acid, and
optionally, thereafter, in any desired sequence, separating isomers and/or liberating blocked hydroxy groups and/or esterifying or etherifying free hydroxy groups and/or oxidizing the aldehyde group and/or esterifying the resultant free carboxy group and/or saponifying an esterified carboxy group or converting a carboxy group into an amide or, with a physiologically compatible base, into a salt.

The reaction of the compound of Formula II with a haloketal of Formula III can be conventionally conducted at temperatures of 0°–100° C., preferably 10°–80° C., in an aprotic solvent or solvent mixture, for example dimethyl sulfoxide, dimethylformamide, tetrahydrofuran, etc. The many suitable bases are known to persons skilled in the art for etherifications, for example sodium hydride, potassium tert-butylate, butyllithium, etc.

The ketal splitting following etherification to obtain the compounds of Formula I takes place according to methods known per se. For example, ketal cleavage can be effected in an aqueous solution of an organic acid, e.g., acetic acid, propionic acid, and others; or in an aqueous solution of any inorganic acid, e.g., hydrochloric acid. To improve solubility, a water-miscible, inert organic solvent is suitably added. Organic solvents that can be used include for example, alcohols, such as methanol and ethanol, and ethers, such as dimethyoxyethane, dioxane, and tetrahydrofuran. Tetrahydrofuran is preferably employed. The ketal cleavage is conducted preferably at temperatures of 20° to 80° C.

The aldehyde group can be oxidized by methods known to those skilled in the art. Examples for suitable oxidizing agents are: pyridinium dichromate (Tetrahedron Letters 1979 : 399), Jones reagent (J. Chem. Soc. 1953 : 2555) or platinum/oxygen (Adv. in Carbohydrate Chem. 17 : 169 [1962]).

Oxidation with pyridinium dichromate is conducted at temperatures at 0°–100° C., preferably 20°–40° C., in a solvent inert with respect to the oxidizing agent, for example dimethylformamide.

Oxidation with Jones reagent is effected at temperatures of −40° C. to +40° C., preferably 0–30° C., in acetone as the solvent. Oxidation with platinum/oxygen is carried out at temperatures of 0°–60° C., preferably 0°–40° C., in a solvent inert with respect to the oxidizing agent, such as, for example, ethyl acetate.

The saponification of the carbacyclin esters can be conducted according to methods known to those skilled in the art, such as, for example, using alkaline catalysts.

The introduction of the ester group —$OR_2$ as $R_1$, wherein $R_2$ is an alkyl group of 1-10 carbon atoms also takes place according to methods known to persons skilled in the art. The carboxy compounds can be reacted, for example, with diazohydrocarbons in a manner known per se. Esterification with diazohydrocarbons is effected, for example, by mixing a solution of the diazohydrocabon in an inert solvent, preferably in diethyl ether, with the carboxy compound in the same or a different inert solvent, e.g., methylene chloride, After the reaction is completed within 1-30 minutes, the solvent is removed and the ester purified as usual. Diazoalkanes are either known or can be produced by known methods [Org. Reactions 8 : 389-394 (1954)].

The introduction of the ester group —$OR_2$ as $R_1$ wherein $R_2$ is a substituted or unsubstituted aryl group also takes place by means of methods known to one skilled in the art. For example, the carboxy compounds and the corresponding arylhydroxy compounds can be reacted with dicyclohexylcarbodiimide in the presence of a suitable base, e.g., pyridine or triethylamine, in an inert solvent. The many suitable solvents include methylene chloride, ethylene chloride, chloroform, ethyl acetate, tetrahydrofuran, preferably chloroform. The reaction is conducted at temperatures of −30° to +50° C., preferably at +10° C.

The ester group —$OR_2$ as $R_1$ wherein $R_2$ is

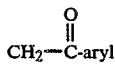

aryl can also be introduced by conventionally reacting the carboxylate anion with the corresponding alkyl halogenide or ω-haloketone, especially for

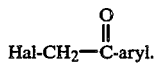

The definition of aryl is already given above.

The compounds containing $OR_2$ groups wherein $R_2$ is cycloalkyl or a heterocyclic residue can be prepared by analogous methods, e.g., to those mentioned for $R_2$ alkyl and aryl groups.

The amide group $NHR_3$ can also be introduced as $R_1$ according to methods known to those skilled in the art. The carboxylic acids of Formula I ($R_2$=H) can first of all be converted into the corresponding mixed anhydride with the isobutyl ester of chloroformic acid. in the presence of a tertiary amine, e.g., triethylamine. The mixed anhydride is reacted with the alkali metal salt of the corresponding amide or with ammonia ($R_3$=H) in an inert solvent or solvent mixture, e.g., tetrahydrofuran, dimethoxyethane, dimethylformamide, hexamethylphosphoric triamide, at temperatures of −30° to +60° C., preferably at 0°-30° C.

Another method for introducing the amide group $NHR_3$ as $R_1$ involves reacting a 1-carboxylic acid of Formula I ($R_2$=H) wherein free hydroxy groups are optionally blocked intermediarily, with compounds of Formula IV $$O=C=N-R_3 \quad \text{IV}$$

wherein $R_3$ is as defined above.

The reaction of the compound of Formula I ($R_1$=OH) with an isocyanate of Formula IV takes place, optionally, with the addition of a tertiary amine, such as, for example, triethylamine or pyridine. The reaction can be accomplished without a solvent or in an inert solvent, preferably acetonitrile, tetrahydrofuran, acetone, dimethylacetamide, methylene chloride, diethyl ether, toluene, etc., at temperatures of −80° to 100° C., preferably at 0°-30° C.

If the starting compound contains OH-groups in the prostane residue, these OH-groups will also react. If, in the final analysis, end products are desired containing free hydroxy groups in the prostane moiety, then starting compounds are suitably employed wherein the OH groups are intermediarily blocked preferably by readily cleavable ether or acyl residues.

The carbacyclin derivatives of Formula I wherein $R_1$ is hydroxy ($R_2$=H) can be converted into salts with suitable amounts of the corresponding inorganic bases under conventional neutralizing conditions. For example, the solid inorganic salt is obtained when the corresponding acids are dissolved in water containing a stoichiometric quantity of the base, followed by evaporation of the water or addition of a water-miscible solvent, e.g., alcohol or acetone.

Amine salts are also prepared as usual. For this purpose, the carbacyclin acid can be dissolved, for example, in a suitable solvent such as ethanol, acetone, diethyl ether, or benzene, and at least a stoichiometric amount of the amine is added to this solution. During this step, the salt is ordinarily obtained in the solid phase or is isolated as usual after evaporation of the solvent.

The functional modification of the free OH-groups is conducted according to methods known to persons skilled in the art. For example, in order to introduce ether blocking groups, the reaction is carried out, e.g., with dihydropyran in methylene chloride or chloroform with the use of an acidic condensation agent, e.g., p-toluenesulfonic acid. Dihydropyran is used in excess, preferably in four to ten times the amount required theoretically. The reaction is normally completed at 0°-30° C. after 15-30 minutes.

Acyl blocking groups are also conventionally introduced, e.g., by reacting a compound of Formula I with a carboxylic acid derivative, for example an acid chloride, acid anhydride, etc.

The liberation of a functionally modified OH-group to obtain the compounds of Formula I again takes place by methods known per se. For example, ether blocking groups can be split off in an aqueous solution of an anorganic acid, such as, for example, acetic acid, propionic acid, etc., or in an aqueous solution of an organic acid, e.g., hydrochloric acid. In order to improve solubility, a water-miscible, inert organic solvent is suitably added. Suitable organic solvents include, for example, alcohols, such as methanol and ethanol, and ethers, such as dimethoxyethane, dioxane, and tetrahydrofuran. Tetrahydrofuran is preferably employed. The splitting-off step is conducted preferably at temperatures of 20° to 80° C.

The silyl ether blocking groups are split off, for example, with tetrabutylammonium fluoride. Examples of suitable solvents include tetrahydrofuran, diethyl ether, dioxane, methylene chloride, etc. The splitting-off step is preferably conducted at temperatures of 0° to 80° C.

The acyl groups are saponified, for example, with alkali or alkaline earth metal carbonates or hydroxides in an alcohol or in the aqueous solution of an alcohol. Suitable alcohols are aliphatic alcohols, e.g., methanol, ethanol, butanol, etc., preferably methanol. Alkali metal carbonates and hydroxides that can be mentioned include potassium and sodium salts, but the potassium salts are preferred. Suitable alkaline earth metal carbonates and hydroxides include, for example calcium carbonate, calcium hydroxide, and barium carbonate. The reaction takes place at $-10°$ to $70°$ C., preferably at $25°$ C.

The starting materials of Formula II can be prepared, for example, by conventionally reacting an aldehyde of Formula V (DOS 2,845,770)

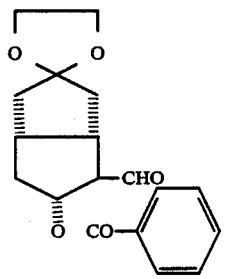

V with a phosphonate of Formula VI

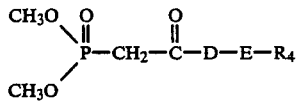

VI wherein D, E, and $R_4$ are as defined above, in the presence of a deprotonating agent, e.g., sodium hydride or potassium tert-butylate, to obtain a ketone of Formula VII (X=H) or additionally, in the presence of a brominating agent, for example N-bromosuccinimide, to a ketone of Formula VII (X=Br):

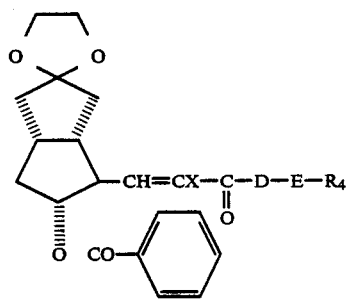

VII

After conventional reduction of the keto group with zinc borohydride or sodium borohydride or reaction with alkyl magnesium bromide or alkyl lithium and subsequent separation of epimers, the compounds of Formula VIII are obtained:

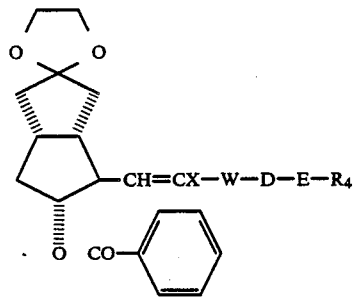

VIII

By saponification of the ester group, for example with potassium carbonate in methanol, as well as, optionally, hydrogenation of the double bond or, optionally, etherification with dihydropyran and subsequent splitting off of hydrogen bromide with, for example, potassium tert-butylate in dimethyl sulfoxide, ketal splitting with aqueous acetic acid, as well as, optionally, functional modification of the free hydroxy groups, for example by etherification with dihydropyran, the ketones of Formula IX are obtained:

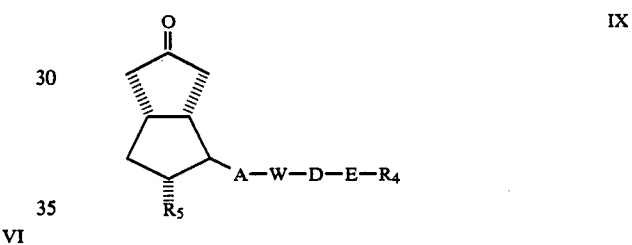

IX

After a conventional olefin-forming reaction with phosphonofluoroacetic acid triethyl ester or phosphonofluoroacetic acid trimethyl ester, and subsequent reduction with lithium aluminum hydride, the compounds of Formula II isomeric in the double bond are obtained. These can optionally be separated.

The phosphonates of Formula VI can be produced in a manner known per se by reacting the anion of the dimethyl ester of methylphosphonic acid with an ester of Formula X

X wherein

D, E, $R_4$ are as defined above and $R_8$ is an alkyl group of 1-5 carbon atoms.

This ester can be conventionally obtained, if desired, from the corresponding malonic acid ester by alkylation with a halogenide of Formula XI:

Hal—E—$R_4$  XI wherein Hal is chlorine or bromine, and subsequent decarbalkoxylation. The ester of Formula X is also conventionally obtainable, if desired, from the carboxylic acid of Formula XII

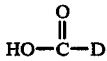
                                                        XII wherein D is as defined above, by alkylation with the halogenide of Formula XI and subsequent esterification.

The starting material compounds of Formula III can be prepared, for example, by conventionally reducing an ω-halocarboxylic acid ester of Formula XIII:

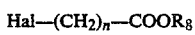                                    XIII wherein

Hal and n are as defined above and $R_8$ is an alkyl group of 1–5 carbon atoms, with diisobutyl aluminum hydride to the corresponding aldehyde and subsequently ketalizing the product conventionally with an alcohol.

As can be seen, all of the starting materials required for the preparation of the compounds of this invention are known or readily preparable using fully conventional techniques.

The compounds of this invention have bloodpressure-lowering and bronchodilatory effects. They are furthermore suitable for inhibiting thrombocyte aggregation. Consequently, the novel carbacyclin derivatives of Formula I represent valuable pharmacologically active agents. Moreover, with a similar spectrum of activity, they exhibit a higher specificity as compared with corresponding prostaglandins and, above all, a substantially longer efficacy. As compared with $PGI_2$, they are distinguished by higher stability.

The high tissue specificity of the novel prostaglandins is demonstrated in a study on smooth-muscle organs, such as, for example, on the guinea pig ileum or on the isolated rabbit trachea, where a substantially lower stimulation can be observed than in the administration of natural prostaglandins of the E-, A-, or F-type.

The novel carbacyclin analogs also exhibit the properties typical for prostacyclins, such as, for example, lowering of peripheral arterial and coronary vascular resistance, inhibition of thrombocyte aggregation and dissolution of platelet thrombi, myocardial cytoprotection and thus lowering of systemic blood pressure without simultaneously lowering stroke volume and coronary blood flow; treatment for stroke, prophylaxis and therapy of coronary heart disease, coronary thrombosis, cardiac infarction, peripheral arterial diseases, arteriosclerosis and thrombosis, prophylaxis and therapy of ischemic attacks of the CNS system, therapy for shock, inhibition of bronchoconstriction, inhibition of gastric acid secretion, cytoprotection for gastric and intestinal mucosa, cytoprotection in liver and pancreas, anti-allergic properties, lowering of pulmonary vascular resistance and pulmonary blood pressure, promotion of kidney blood flow, utilization in place of heparin or as an adjuvant in dialysis of hemofiltration, preservation of blood plasma stores, especially blood platelet stores, inhibition of labor, treatment of gestational toxicosis, enhancement of cerebral blood flow, etc. In addition, the novel carbacyclin derivatives exhibit antiproliferative and antidiarrheogenic properties. The carbacyclins of this invention can also be utilized in combination, for example with β-blockers or diuretics.

The novel prostaglandin analogs of this invention are substantially more selective with regard to potency, as compared with known PG analogs, in causing prostaglandinlike biological responses, and have a substantially longer duration of biological activity. Accordingly, each of these novel prostaglandin analogs is surprisingly and unexpectedly more useful than one of the corresponding conventional prostaglandin-type compounds for at least one of the pharmacological purposes indicated above, because it has a different and narrower spectrum of biological potency than the known prostaglandin, and therefore is more specific in its activity and causes smaller and fewer undesired side effects than when the prostaglandin is used for the same purpose. Moreover, because of its prolonged activity, fewer and smaller doses of the novel prostaglandin analog are frequently effective in attaining the desired result.

The usual dosage of the compounds is 1–1,500 μg/kg/day when administered to human patients. The unit dosage for the pharmaceutically acceptable carrier is usually 0.01–100 mg. Precise dosages in a given case can be readily determined using fully conventional methods, e.g., by differential potency tests vis a vis a known analogous agent such as $PGI_2$. In general, the administration of the compounds of this invention will be analogous to that of a related known agent, e.g., $PGI_2$.

Upon intravenous injection administered to nonanesthetized, hypertonic rats in doses of 5, 20, and 100 μg/kg/body weight, the compounds of this invention exhibit a stronger blood-pressure-lowering effect and a more prolonged duration of efficacy than $PGE_2$ and $PGA_2$ without triggering diarrhea, as does $PGE_2$, or cardiac arrhythmias, as does $PGA_2$.

Upon intravenous injection administered to narcotized rabbits, the compounds of this invention show, as compared with $PGE_2$ and $PGA_2$, a stronger and also considerably prolonged blood-pressure-lowering effect without affecting other smooth-muscle organs or organ functions.

Sterile, injectable, aqueous or oily solutions are used for parenteral administration. Suitable for oral administration are, for example, tablets, dragees, or capsules. The invention accordingly also concerns medicinal agents based on the compounds of Formula I and conventional auxiliary agents and excipients. Thus, the active agents of this invention can serve, in conjunction with the excipients known and customary in galenic pharmacy, for example for the preparation of bloodpressure-lowering agents or agents corresponding to the many other uses of this invention.

The pharmacologically active compounds of this invention can be processed in accordance with conventional methods of galenic pharmacy to produce medicinal agents, especially for oral administration. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampules are convenient unit dosages.

For enteral application, particuarly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(5E)-(16RS)-2-Decarboxy-1a,1b-dihomo-2-formyl-16-methyl-3-oxa-18,18,19,19-tetradehydro-6a-carbaprostaglandin $I_2$ At 0° C., 77 mg of 55% sodium hydride suspension in mineral oil is added to a solution of 700 mg of 2-[(E)-(1S,5S,6R,7R)-7-(tetrahydropyran -2-yloxy)-6-[(E)-(3S,4RS)-4-methyl-3-(tetrahydropyran-2-yloxy) oct-1-en-6-ynyl]bicyclo[3.3.0]octan-3-ylidene]ethan-1-ol in 15 ml of tetrahydrofuran; the mixture is agitated for 30 minutes at 24° C. under argon. Then a solution of 1.15 g of 2-(3-bromopropyl)-1,3-dioxolane in 7 ml of tetrahydrofuran is added dropwise thereto and the mixture is refluxed for 21 hours under argon. Then the mixture is diluted with ether, washed neutral with water, dried over magnesium sulfate, and evaporated under vacuum. Chromatography of the residue on silica gel yields, with hexane/ether (7+3), 480 mg of the oxa compound which is stirred for 16 hours at 24° C. with 40 ml of a mixture of acetic acid/water/tetrahydrofuran (65/35/10). Then the mixture is evaporated under vacuum and the residue is chromatographed on silica gel. With ethyl acetate/hexane (4+1), 270 mg of the title compound is obtained as a colorless oil.

IR ($CHCl_3$) 3600, 3420 (broad), 2970, 2862, 2730, 1725, 1603, 970 $cm^{-1}$.

2-(3-Bromopropyl)-1,3-dioxolane, utilized for the above etherification, is prepared as follows:

At $-70°$ C., 50 ml of a 1.2-molar solution of diisobutyl aluminum hydride in toluene is added dropwise gradually to a solution of 9.6 g of the ethyl ester of bromobutyric acid in 595 ml of toluene; the mixture is stirred for 15 minutes at $-70°$ C. and then combined dropwise with 10 ml of isopropyl alcohol and 25 ml of water. The mixture is agitated for 2 hours at room temperature, filtered, the filtrate dried with magnesium sulfate and evaporated under vacuum at 25° C. The residue is dissolved in 500 ml of toluene, 10 ml of ethylene glycol and 100 mg of p-toluenesulfonic acid are added, and the mixture is refluxed for 6 hours with the use of a water trap. Subsequently the mixture is diluted with 500 ml of ether, shaken once with a 5% sodium bicarbonate solution and three times with water, the organic extract is dried with magnesium sulfate and concentrated under vacuum at 30° C. Distillation of the residue at 0.6 torr and 43°–45° C. yields 6.8 g of 2-(3-bromopropyl)-1,3-dioxolane as a colorless liquid.

EXAMPLE 2

(5E)-(16RS)-1a,1b-Dihomo-16-methyl-3-oxa-18,18,19,19-tetradehydro-6a-carbaprostaglandin $I_2$ A solution of 500 mg of the aldehyde prepared according to Example 1 in 5 ml of pyridine is combined with 2 ml of acetic anhydride; the mixture is allowed to stand for 18 hours at room temperature. Subsequently the mixture is concentrated under vacuum, the resultant 11,15-diacetate is dissolved in 25 ml of acetone and combined at 0° C. dropwise with 2.1 ml of Jones reagent. The mixture is then stirred for 30 minutes at 0° C., 2 ml of isopropyl alcohol is added, the mixture is diluted with ether, shaken three times with water, dried over magnesium sulfate, and evaporated under vacuum. Chromatography of the residue on silica gel with hexane/ethyl acetate (1+1) yields 410 mg of (5E)-(16RS)-1a,1b-dihomo16-methyl-3-oxa-18,18,19,19-tetradehydro-6a-carbaprostaglandin $I_2$ 11,15-diacetate as a colorless oil.

IR: 3650, 3400 (broad), 2960, 1730, 1600, 1245, 968 $cm^{-1}$.

In order to split off the blocking groups, 410 mg of the 11,15-diacetate in 20 ml of methanol is agitated for 16 hours at 24° C. with 520 mg of potassium carbonate. Then the mixture is concentrated under vacuum, acidified with 10% citric acid solution to pH 4, extracted three times with methylene chloride, washed twice with water, dried over magnesium sulfate, and evaporated under vacuum. The residue is chromatographed with ethyl acetate/acetic acid (99.5+0.5) on silica gel, thus obtaining 305 mg of the title compound as a colorless oil.

IR: 3590, 3420 (broad), 2960, 2930, 2865, 1720, 1600, 970 $cm^{-1}$.

EXAMPLE 3

(5Z)-(16RS)-2-Decarboxy-1a,1b-dihomo-2-formyl16-methyl-3-oxa-18,18,19,19-tetradehydro-6a-carbaprostaglandin $I_2$ Analogously to Example 1, 320 mg of 2-[(Z)-(1S,5S,6R,7R)-7-(tetrahydropyran-2-yloxy) -6-[(E)-(3S,4RS)-4-methyl-3-(tetrahydropyran-2-yloxy) oct-1-en-6-ynyl]bicyclo[3.3.0]octan-3-ylidene]ethan-1-ol yields 125 mg of the title compound as a colorless oil.

IR: 3610, 3400 (broad), 2965, 2860, 2730, 1726, 1602, 968 $cm^{-1}$.

EXAMPLE 4

(5Z)-(16RS)-1a,1b-Dihomo16-methyl-3-oxa-18,18,19,19-tetradehydro-6a-carbaprostaglandin $I_2$ Analogously to Example 2, 125 mg of the aldehyde prepared according to Example 3 yields 90 mg of (5Z)-(16RS)-1a,1b-dihomo-16-methyl-3-oxa-18,18,19,19-tetradehydro-6a-carbaprostaglandin $I_2$ 11,15-diacetate. After splitting off the blocking groups, 57 mg of the title compound is obtained as a colorless oil.

IR: 3600, 3410 (broad), 2960, 2866, 1718, 1600, 968 $cm^{-1}$.

EXAMPLE 5

(5E)-(16RS)-2-Decarboxy-1a,1b-dihomo-16,20-dimethyl-2-formyl-3-oxa-18,18,19,19-tetradehydro-6a-carbaprostaglandin $I_2$ In analogy to Example 1, 1.35 g of 2-[(E)-(1S,5S,6R,7R)-7-(tetrahydropyran-2-yloxy)-6-[(E)-(3S,4RS)-4-methyl-3-(tetrahydropyran-2-yloxy) non-1-en-6-ynyl]bicyclo[3.3.0]octan-3-ylidene]ethan-1-ol yields 610 mg of the title compound as a colorless oil.

IR: 3600, 3410 (broad), 2967, 2862, 2731, 1725, 1601, 970 cm$^{-1}$.

The starting material for the above title compound is produced as follows:

5(a)
(1R,5S,6R,7R)-3,3-Ethylenedioxy-7-benzoyloxy-6-[(E)-(3S,4RS)
-3-hydroxy-4-methylnon-1-en-6-ynyl]bicyclo[3.3.0]octane At 0° C., a solution of 9.02 g of 3-methyl-2-oxooct-5-ynylphosphonic acid dimethyl ester in 67 ml of dimethoxyethane (DME) is added dropwise to a suspension of 1.46 g of sodium hydride (55% strength suspension in oil) in 130 ml of DME, and the mixture is stirred for one hour at 0° C. Then, at −20° C., the mixture is combined with a solution of 9.4 g of (1R,5S,6R,7R)-3,3-ethylenedioxy-7-benzoyloxy-6-formylbicyclo [3.3.0]octane in 130 ml of DME, agitated for 1.5 hours at −20° C., poured on 600 ml of saturated ammonium chloride solution, and extracted three times with ether. The organic extract is washed neutral with water, dried over magnesium sulfate, and evaporated under vacuum. Chromatography of the residue on silica gel yields, with ether/hexane (1+1), 9.1 g of the α,β-unsaturated ketone as an oil.

At −40° C., 5.2 g of sodium borohydride is added in incremental portions to a solution of 9.1 g of the ketone in 300 ml of methanol; the mixture is stirred for one hour at −40° C., then diluted with ether, washed neutral with water, dried over magnesium sulfate, and evaporated under vacuum. Column chromatography on silica gel with ether/hexane yields first of all 3.9 g of the title compound (PG nomenclature: 15α-hydroxy) and, as the more polar component, 3.2 g of the isomeric 15β-hydroxy compound.

IR: 3600, 3400 (broad), 2942, 1711, 1603, 1588, 1276, 968, 947 cm$^{-1}$.

5(b)
(1R,5S,6R,7R)-7-(Tetrahydropyran-2-yloxy)-6-[(E)-(3S,4RS)
-3-(tetrahydropyran-2-yloxy)-4-methylnon-1-en-6-ynyl]bicyclo[3.3.0]-octan-3-one A mixture of 3.6 g of the α-alcohol prepared according to Example 5(a) and 1.4 g of potassium carbonate in 120 ml of methanol is agitated for 16 hours at room temperature under argon. Subsequently the mixture is concentrated under vacuum, diluted with ether, and washed neutral with brine. The mixture is dried over magnesium sulfate and evaporated under vacuum. The evaporation residue is stirred for 16 hours at room temperature with 75 ml of a mixture of acetic acid/water/tetrahydrofuran (65/35/10) and then evaporated under vacuum. Filtration of the residue over silica gel yields, with ethyl acetate/hexane (7+3), 2.2 g of the ketone as an oil.

A solution of 2.2 g of the ketone, 2.4 ml of dihydropyran, and 23 mg of p-toluenesulfonic acid in 75 ml of methylene chloride is agitated for 30 minutes at 0° C., then diluted with ether, shaken with dilute sodium bicarbonate solution, washed neutral with water, dried over magnesium sulfate, and evaporated under vacuum, thus obtaining 3.4 g of the bistetrahydropyranyl ether which is used without purification.

IR: 2960, 2865, 1738, 970 cm$^{-1}$.

5(c)
2-[(E)-(1S,5S,6R,7R)-7-(Tetrahydropyran-2-yloxy)-6-[(E)-(3S,4RS)
-4-methyl-3-(tetrahydropyran-2-yloxy)non-1-en-6-ynyl]bicyclo[3.3.0]octan-3-ylidene]ethan-1-ol At 0° C., 3.5 g of potassium tert-butylate is added to a solution of 8.1 g of phosphonoacetic acid triethyl ester in 170 ml of tetrahydrofuran; the mixture is agitated for 10 minutes, combined with a solution of 9 g of the ketone prepared according to Example 5(b) in 90 ml of toluene, and stirred for 16 hours at room temperature under argon. The mixture is diluted with 1,000 ml of ether, shaken neutral with water, dried over magnesium sulfate, and evaporated under vacuum. The residue is filtered with hexane/ether (3+2) over silica gel, thus producing 8.2 g of the unsaturated ester as a colorless oil.

IR: 2950, 2870, 1700, 1655, 968 cm$^{-1}$.

At 0° C., 2.2 g of lithium aluminum hydride is added in incremental portions to a stirred solution of 8 g of the ester as prepared above in 280 ml of ether and agitated for 30 minutes at 0° C. Excess reagent is destroyed by dropwise addition of ethyl acetate, 12 ml of water is added, and the mixture is stirred for 2 hours at 22° C., filtered, and evaporated under vacuum. The residue is chromatographed with ether/hexane (3+2) on silica gel, thus obtaining, as the less polar compound, 2.8 g of 2-[(Z)-(1S,5S,6R,7R)-7-(tetrahydropyran-2-yloxy)-6-[(E)-(3S,4RS)-4-methyl-3-(tetrahydropyran-2-yloxy)non-1-en-6-ynyl]bicyclo[3.3.0]octan-3-ylidene]ethan-1-ol and 4.2 g of the title compound as a colorless oil.

IR: 3600, 3430, 2942, 2863, 1600, 972 cm$^{-1}$.

EXAMPLE 6

(5E)-(16RS)-1a,1b-Dihomo-16,20-dimethyl-3-oxa18,18,19,19-tetradehydro -6a-carbaprostaglandin $I_2$ In analogy to Example 2, 380 mg of the aldehyde prepared according to Example 5 yields 305 mg of (5E)-(16RS)-1a,1b-dihomo-16,20-dimethyl-3-oxa-18,18,19,19-tetradehydro-6a-carbaprostaglandin $I_2$ 11,15-diacetate. After the blocking groups have been split off, 210 mg of the title compound is obtained as a colorless oil.

IR: 3600, 3400 (broad), 2962, 2865, 1720, 1601, 970 cm$^{-1}$.

EXAMPLE 7

(5E)-2-Decarboxy-1a,1b-dihomo-2-formyl-20-methyl-3-oxa-16,16-trimethylene
-18,18,19,19-tetradehydro-6a-carbaprostaglandin $I_2$ Analogously to Examples 1 and 5, 0.9 g of 2-[(E)-(1S,5S,6R,7R)-7-(tetrahydropyran-2-6-[(E)-(3R)-3-(tetrahydropyran-2-yloxy)-4,4-trimethylene-non-1-en-6-ynyl]-bicyclo[3.3.0]octan-3-ylidene]ethan-1-ol (prepared according to Examples 5(a)–5(c) from 2-oxa-3,3- trimethylene-non-5-ynephosphonic acid dimethyl ester) produces 0.4 g of the title compound as a colorless oil.

IR: 3610, 3400 (broad), 2968, 2864, 2730, 1725, 1602, 970 cm$^{-1}$.

The starting material for the above title compound is prepared as set forth below

7(a)
2-[(E)-(1S,5S,6R,7R)-7-(Tetrahydropyran-2-yloxy)-4,4-trimethylene -non-1-en-6-ynyl]-bicyclo[3.3.0]octan-3-ylidene]ethan-1-ol Analogously to Example 5(c), 3 g of (1R,5S,6R,7R)-7-(tetrahydropyran-2-yloxy)-6-[(E)-(3R)-3-(tetrahydropyran-2-yloxy) -4,4-trimethylene-non-1-en-6-ynyl]bicyclo[3.3.0]octan-3-one yields, after separation of isomers by chromatography, as the less polar compound 470 mg of 2-[(Z)-(1S,5S,6R,7R)-7-(tetrahydropyran-2-yloxy)-4,4-trimethylene-non-1-en-6-ynyl]bicyclo[3.3.0]octan-3-ylidene]ethan-1-ol and 690 mg of the title compound as a colorless oil.

IR: 3600, 3400 (broad), 2945, 2862, 1602, 972 cm$^{-1}$.

EXAMPLE 8

(5E)-1a,1b-Dihomo-20-methyl-3-oxa-16,16-trimethylene-18,18,19,19-tetradehydro-6a-carbaprostaglandin I$_2$ In analogy to Example 2, 400 mg of the aldehyde prepared according to Example 7 yields 295 mg of (5E)-1a,1b-dihomo-20-methyl-3-oxa -16,16-trimethylene-18,18,19,19- tetradehydro-6a-carbaprostaglandin I$_2$ 11,15-diacetate. After the blocking groups have been split off, 220 mg of the title compound is obtained as a colorless oil.

IR: 3610, 3400 (broad), 2960, 2864, 1721, 1602, 970 cm$^{-1}$.

EXAMPLE 9

(5E)-2-Decarboxy-1a,1b-dihomo-16,16-dimethyl-2-formyl-3-oxa -18,18,19,19-tetradehydro-6a-carbaprostaglandin I$_2$ In analogy to Examples 1 and 5, 0.5 g of 2-[(E)(1S,5S,6R,7R) -7-(tetrahydropyran-2-yloxy)-6-[(E)-(3R)-4,4-dimethyl-3-(tetrahydropyran-2-yloxy) oct-1-en-6-ynyl]bicyclo[3.3.0]octan-3-ylidene]ethan-1-ol yields 0.28 g of the title compound as a colorless oil.

IR: 3600, 3400 (broad), 2965, 2732, 1724, 1600, 970 cm$^{-1}$.

EXAMPLE 10

(5E)-1a,1b-Dihomo-16,16-dimethyl-3-oxa-18,18,19,19-tetradehydro-6a-carbaprostaglandin I$_2$ Analogously to Example 2, 0.27 g of the aldehyde obtained according to Example 9 yields 180 mg of (5E)-1a,1b-dihomo-16,16-dimethyl-3-oxa-18,18,19,19-tetradehydro-6a-carbaprostaglandin I$_2$ 11,15-diacetate. After the blocking groups have been split off, 120 mg of the title compound is obtained as a colorless oil.

IR: 3600, 3400 (broad), 2962, 2865, 1720, 1600, 971 cm$^{-1}$.

EXAMPLE 11

(5E)-2-Decarboxy-1a,1b-dihomo-2-formyl-3-oxa-16,16,20-trimethyl -18,18,19,19-tetradehydro-6a-carbaprostaglandin I$_2$ Analogously to Examples 1 and 5, 1.1 g of 2-[(E)-(1S,5S,6R,7R) -7-(tetrahydropyran-2-yloxy)-6-[(E)-(3R)-4,4-dimethyl-3-(tetrahydropyran-2-yloxy) non-1-en-6-ynyl]bicyclo[3.3.0]octan-3-ylidene]ethan-1-ol produces 0.6 g of the title compound as a colorless oil.

IR: 3610, 3420 (broad), 2964, 2730, 1725, 1602, 972 cm$^{-1}$.

EXAMPLE 12

(5E)-1a,1b-Dihomo-3-oxa-16,16,20-trimethyl-(18,18,19,19-tetradehydro -6a-carbaprostaglandin I$_2$ Analogously to Example 2, 0.4 g of the aldehyde prepared as described in Example 11 yields 0.3 g of (5E)-1a,1b-dihomo-3-oxa-16,16,20-trimethyl-18,18,19,19-tetradehydro-6a-carbaprostaglandin I$_2$ 11,15-diacetate. After splitting off the blocking groups, 0.22 g of the title compound is obtained as a colorless oil.

IR: 3610, 3400 (broad), 2964, 2864, 1721, 1600, 972 cm$^{-1}$.

EXAMPLE 13

(5E)-(16RS)-2-Decarboxy-18,19-didehydro-1a,1b-dihomo-16,19-dimethyl -2-formyl-3-oxa-6a-carbaprostaglandin I$_2$ Analogously to Examples 1 and 5, 0.7 g of 2-[(E)-(1S,5S,6R,7R) -7-(tetrahydropyran-2-yloxy)-6-[(E)-(3S,4RS)-4,7-dimethyl-3-(tetrahydropyran -2-yloxy)oct-1,6-dienyl]-bicyclo[3.3.0]octan-3-ylidene]ethan-1-ol produces 0.4 g of the title compound as a colorless oil.

IR: 3600, 3400 (broad), 2966, 2732, 1725, 1601, 972 cm$^{-1}$.

EXAMPLE 14

(5E)-1a,1b-Dihomo16,19-dimethyl-18,19-didehydro-3-oxa-6a-carbaprostaglandin I$_2$ In analogy to Example 2, 0.2 g of the aldehyde prepared according to Example 13 yields 0.14 g of (5E)-1a,1b-dihomo-16,19-dimethyl-18,19-didehydro-3-oxa-6a-carbaprostaglandin I$_2$ 11,15-diacetate. After the blocking groups have been split off, 90 mg of the title compound is obtained as a colorless oil.

IR: 3600, 3410 (broad), 2960, 2860, 1720, 1601, 972 cm$^{-1}$.

EXAMPLE 15

(5E)-(16RS)-2-Decarboxy-13,14-didehydro-1a,1b-dihomo-2-formyl -16-methyl-3-oxa-18,18,19,19-tetradehydro-6a-carbaprostaglandin I$_2$ Analogously to Examples 1 and 5, 0.6 g of 2-[(E)-(1S,5S,6S,7R) -7-(tetrahydropyran-2-yloxy)-6-[(3S,4RS)-4-methyl-3-(tetrahydropyran-2-yloxy) octa-1,6-diynyl]bicyclo [3.3.0]octan-3-ylidene]ethan-1-ol yields 0.29 g of the title compound as a colorless oil.

IR: 3610, 3410 (broad), 2966, 2730, 2225, 1725 cm$^{-1}$.

The starting material for the above title compound is produced as follows:

15(a)
2-[(E)-(1S,5S,6S,7R)-7-(Tetrahydropyran-2-yloxy)-6-[(3S,4RS) -4-methyl-3-(tetrahydropyran-2-yloxy)octa-1,6-diynyl]-bicyclo[3.3.0]octan-3-ylidene]ethan-1-ol Analogously to Example 5(c), 1.8 g of (1R,5S,6S,7R)-7-(tetrahydropyran-2-yloxy)-6-

[(3S,4RS)-4-methyl-3-(tetrahydropyran-2-yloxy)octa-1,6-diynyl]bicyclo [3.3.0]octan-3-one yields, after isomer separation by chromatography, as the less polar compound 380 mg of 2-[(Z)-(1S,5S,6S,7R)-7-(tetrahydropyran-2-yloxy)-6-[(3S,4RS)-4-methyl-3-(tetrahydropyran-2-yloxy)octa-1,6-diynyl]bicyclo [3.3.0]octan-3-ylidene]ethan-1-ol and 610 mg of the title compound as an oil.

IR: 3600, 3400 (broad), 2945, 2860, 2225 cm$^{-1}$.

EXAMPLE 16

(5E)-(16RS)-13,14-Didehydro-1a,1b-dihomo16-methyl-3-oxa-18,18,19,19-tetradehydro-6a-carbaprostaglandin $I_2$ Analogously to Example 2, 0.4 g of the aldehyde prepared as disclosed in Example 15 yields 0.21 g of (5E)-(16RS)-13,14-didehydro -1a,1b-dihomo16-methyl-3-oxa-18,18,19,19-tetradehydro-6a-carbaprostaglandin $I_2$ 11,15-diacetate. After the blocking groups have been split off, 150 mg of the title compound is obtained in the form of a colorless oil.

IR: 3600, 3410 (broad), 2960, 2864, 2226, 1718 cm$^{-1}$.

EXAMPLE 17

(5E)-(16RS)-2-Decarboxy-13,14-didehydro-1a,1b-dihomo-16,20-dimethyl-2-formyl-3-oxa-18,18,19,19-tetradehydro-6a-carbaprostaglandin $I_2$ In analogy to Examples 1 and 5, 0.8 g of 2-[(E)-(1S,5S,6S,7R)-7-(tetrahydropyran-2-yloxy)-6-[(3S,4RS)-4-methyl-3-(tetrahydropyran-2-yloxy)nona-1,6-diynyl]bicyclo [3.3.0]octan-3-ylidene]ethan-1-ol yields 0.42 g of the title compound as a colorless oil.

IR: 3600, 3400 (broad), 2965, 2732, 2227, 1724 cm$^{-1}$.

The starting material for the above title compound is prepared as follows:

17(a)

2-[(E)-(1S,5S,6S,7R)-7-(Tetrahydropyran-2-yloxy)-6-[(3S,4RS)-4-methyl-3-(tetrahydropyran-2-yloxy)nona-1,6-diynyl]bicyclo[3.3.0]octan-3-ylidene]ethan-1-ol In analogy to Example 5(c), 2.1 g of (1R,5S,6S,7R)-7-(tetrahydropyran-2-yloxy)-6-[(3S,4RS)-4-methyl-3-(tetrahydropyran-2-yloxy)nona-1,6-diynyl]bicyclo [3.3.0]octan-3-one yields, after chromatographic separation of isomers, as the less polar compound 450 mg of 2-[(Z)-(1S,5S,6S,7R)-7-(tetrahydropyran-2-yloxy)-6-[(3S,4RS)-methyl-3-(tetrahydropyran-2-yloxy)nona-1,6-diynyl]bicyclo [3.3.0]octan-3-ylidene]ethan-1-ol and 740 mg of the title compound as a colorless oil.

IR: 3600, 3420 (broad), 2947, 2862, 2223 cm$^{-1}$.

EXAMPLE 18

(5E)-(16RS)-13,14-Didehydro-1a,1b-dihomo16,20-dimethyl-3-oxa-18,18,19,19-tetradehydro-6a-carbaprostaglandin $I_2$ Analogously to Example 2, 620 mg of the aldehyde produced according to Example 17 yields 340 mg of (5E)-(16RS)-13,14-didehydro-1a,1b -dihomo16,20-dimethyl-3-oxa-18,18,19,19-tetradehydro-6a-carbaprostaglandin $I_2$ 11,15-diacetate. After the blocking groups have been split off, 260 mg of the title compound is obtained as a colorless oil.

IR: 3610, 3400 (broad), 2962, 2865, 2225, 1720 cm$^{-1}$.

EXAMPLE 19

(5E)-2-Decarboxy-13,14-didehydro-1a,1b-dihomo-2-formyl-20-methyl-3-oxa-18,18,19,19-tetradehydro-16,16-trimethylene-6a-carbaprostaglandin $I_2$ Analogously to Examples 1 and 5, 0.41 g of 2-[(E)-(1S,5S,6S,7R)-7-(tetrahydropyran-2-yloxy)-6-[(3S)-(tetrahydropyran-2-yloxy)-4,4-trimethylene-nona-1,6-diynyl]bicyclo [3.3.0]octan-3-ylidene]ethan-1-ol yields 0.18 g of the title compound as a colorless oil.

IR: 3600, 3400 (broad), 2965, 2732, 2227, 1724 cm$^{-1}$.

The starting material for the above title compound is prepared as set forth below:

19(a)

2-[(E)-(1S,5S,6S,7R)-7-(Tetrahydropyran-2-yloxy)-6-[(3S)-3-(tetrahydropyran-2-yloxy)-4,4-trimethylene-nona-1,6-diynyl]bicyclo [3.3.0]octan-3-ylidene]ethan-1-ol In analogy to Example 5(c), 3.1 g of (1R,5S,6S,7R)-7-(tetrahydropyran-2-yloxy)-6-[(3S)-3-(tetrahydropyran-2-yloxy)-4,4-trimethylene-nona-1,6-diynyl]bicyclo [3.3.0]octan-3-one yields, after separation of isomers by chromatography, as the less polar compound 890 mg of 2-[(Z)-(1S,5S,6S,7R)-7-(tetrahydropyran-2-yloxy)-6-[(3RS)-3-(tetrahydropyran-2-yloxy)-4,4-trimethylene-nona-1,6-diynyl]bicyclo [3.3.0]octan-3-ylidene]ethan-1-ol and 1.3 g of the title compound as an oil.

IR: 3610, 3420 (broad), 2945, 2862, 2226 cm$^{-1}$.

EXAMPLE 20

(5E)-13,14-Didehydro-1a,1b-dihomo-20-methyl-3-oxa-18,18,19,19-tetradehydro-16,16-trimethylene-6a-carbaprostaglandin $I_2$ Analogously to Example 2, 0.42 g of the aldehyde prepared according to Example 19 yields 0.32 g of (5E)-13,14-didehydro-1a,1b-dihomo-20-methyl-3-oxa-18,18,19,19-tetradehydro16,16-trimethylene-6a-carbaprostaglandin $I_2$ 11,15-diacetate. After the blocking groups have been split off, 210 mg of the title compound is obtained as a colorless oil.

IR: 3600, 3400 (broad), 2963, 2865, 2225, 1720 cm$^{-1}$.

EXAMPLE 21

(5E)-2-Decarboxy-13,14-didehydro-1a,1b-dihomo-16,16-dimethyl-2-formyl-3-oxa-18,18,19,19-tetradehydro-6a-carbaprostaglandin $I_2$ In analogy to Examples 1 and 5, 0.9 g of 2-[(E)-(1S,5S,6S,7R) -7-(tetrahydropyran-2-yloxy)-6-[(3S)-4,4-dimethyl-(tetrahydropyran-2-yloxy) octa-1,6-diynyl]-bicyclo[3.3.0]octan-3-ylidene]ethan-1-ol yields 0.47 g of the title compound as a colorless oil.

IR: 3600, 3410 (broad), 2966, 2730, 2225, 1725 cm$^{-1}$.

The starting material for the above title compound is produced as set out below:

21(a)

2-[(E)-(1S,5S,6S,7R)-7-(Tetrahydropyran-2-yloxy)-6-[(3S)-4,4-dimethyl-3-(tetrahydropyran-2-yloxy)octa-1,6-diynyl]bicyclo[3.3.0]octan-3-ylidene]ethan-1-ol Analogously to Example 5(c), 2.5 g of (1R,5S,6S,7R)-7-(tetrahydropyran-2-yloxy)-6-[(3S)-4,4-dimethyl -3-(tetrahydropyran-2-yloxy)octa-1,6-diynyl]bicyclo [3.3.0]octan-3-one yields, after separating the isomers by chromatography, as the less polar compound 625 mg of 2-[(Z)-(1S,5S,6S,7R) -7-(tetrahydropyran-2-yloxy)-6-[(3S)-4,4-dimethyl-3-(tetrahydropyran-2-yloxy)octa-1,6-diynyl]bicyclo [3.3.0]octan-3-ylidene]ethan-1-ol and 1.1 g of the title compound as an oil.

IR: 3600, 3400 (broad), 2946, 2865, 2225 cm$^{-1}$.

EXAMPLE 22

(5E)-13,14-Didehydro-1a,1b-dihomo16,16-dimethyl-3-oxa -18,18,19,19-tetradehydro-6a-carbaprostaglandin $I_2$ In analogy to Example 2, 0.31 g of the aldehyde prepared according to Example 21 yields 0.21 g of (5E)-13,14-didehydro -1a,1b-dihomo16,16-dimethyl-3-oxa-18,18,19,19-tetradehydro-6a-carbaprostaglandin $I_2$ 11,15-diacetate. After the blocking groups have been split off, 0.14 g of the title compound is obtained as a colorless oil.

IR: 3600, 3410 (broad), 2964, 2865, 2225, 1720 cm$^{-1}$.

EXAMPLE 23

(5E)-2-Decarboxy-13,14-didehydro-1a,1b-dihomo-2-formyl-3-oxa-18,18,19,19-tetradehydro16,16,20-trimethyl-6a-carbaprostaglandin $I_2$ Analogously to Examples 1 and 5, 0.8 g of 2-[(E)-(1S,5S,6S,7R) -7-(tetrahydropyran-2-yloxy)-6-[(3S)-4,4-dimethyl-3-(tetrahydropyran-2-yloxy)nona-1,6-diynyl]-bicyclo [3.3.0]octan-3-ylidene]ethan-1-ol yields 0.31 g of the title compound as a colorless oil.

IR: 3610, 3420 (broad), 2965, 2730, 2226, 1724 cm$^{-1}$.

The starting material for the above title compound is prepared as follows:

23(a)

2-[(E)-(1S,5S,6S,7R)-7-(Tetrahydropyran-2-yloxy)-6-[(3S) -4,4-dimethyl-3-(tetrahydropyran-2-yloxy)nona-1,6-diynyl]bicyclo [3.3.0]octan-3-ylidene]ethan-1-ol Analogously to Example 5(c), 1.3 g of (1R,5S,6S,7R)-7-(tetrahydropyran-2-yloxy)-6-[(3S)-4,4-dimethyl-3-(tetrahydropyran-2-yloxy)nona-1,6-diynyl]-bicyclo [3.3.0]octan-3-one yields, after separating isomers by chromatography, as the less polar compound 300 mg of 2-[(Z)-(1S,5S,6S,7R) -7-(tetrahydropyran-2-yloxy)-6-[(3S)-4,4- dimethyl-3-(tetrahydropyran-2-yloxy)nona-1,6-diynyl]bicyclo [3.3.0]octan-3-ylidene]ethan-1-ol and 430 mg of the title compound as an oil.

IR: 3610, 3400 (broad), 2945, 2865, 2225 cm$^{-1}$.

EXAMPLE 24

(5E)-13,14-Didehydro-1a,1b-dihomo-3-oxa-18,18,19,19-tetradehydro16,16,20-trimethyl-6a-carbaprostaglandin $I_2$ In analogy to Example 2, 0.16 g of the aldehyde prepared according to Example 23 yields 0.1 g of (5E)-13,14-didehydro -1a,1b-dihomo-3-oxa-18,18,19,19-tetradehydro-16,16,20-trimethyl-6a-carbaprostaglandin $I_2$ 11,15-diacetate.

After the blocking groups have been split off, 60 mg of the title compound is obtained as a colorless oil.

IR: 3600, 3400 (broad), 2965, 2864, 2224, 1718 cm$^{-1}$.

EXAMPLE 25

(5Z)-(16RS)-2-Decarboxy-1a,1b-dihomo-5-fluoro-2-formyl-16-methyl-3-oxa-18,18,19,19-tetradehydro-6a-carbaprostaglandin $I_2$ At 0° C., 42 mg of 55% strength sodium hydride suspension in mineral oil is added to a solution of 420 mg of 2-[(Z)-(1S,5S,6R,7R)-7-(tetrahydropyran-2-yloxy)-6-[(E)-(3S,4RS) -4-methyl-3-(tetrahydropyran-2-yloxy)oct-1-en-6-ynyl]bicyclo [3.3.0]octan-3-ylidene]-2-fluoroethan-1-ol in 8 ml of tetrahydrofuran; the mixture is stirred for 30 minutes at 24° C. under argon. Then a solution of 630 mg of 2-(3-bromopropyl)-13-dioxolane in 8 ml of tetrahydrofuran is added thereto and the mixture is refluxed for 20 hours under argon. The mixture is diluted with ether, washed neutral with water, dried over magnesium sulfate, and evaporated under vacuum. After chromatography of the residue on silica gel, hexane/ether (3+2) yields 340 mg of the oxa compound which is stirred with 30 ml of a mixture of acetic acid/water/tetrahydrofuran (65/35/10) for 16 hours at 24° C. The mixture is then evaporated under vacuum and the residue chromatographed on silica gel. With ethyl acetate/hexane (4+1), 280 mg of the title compound is obtained as a colorless oil.

IR: 3600, 3420 (broad), 2960, 2930, 2870, 2730, 1730, 1603, 970 cm$^{-1}$.

EXAMPLE 26

(5Z)-(16RS)-1a,1b-Dihomo-5-fluoro16-methyl-3-oxa-18,18,19,19-tetradehydro-6a-carbaprostaglandin $I_2$ In analogy to Example 2, 205 mg of the aldehyde prepared as disclosed in Example 25 yields 110 mg of (5Z)-(16RS)-1a,1b-dihomo-5-fluoro16-methyl-3-oxa-18,18,19,19-tetradehydro-6a-carbaprostaglandin $I_2$ 11,15-diacetate. After splitting off the blocking groups, 78 mg of the title compound is obtained as a colorless oil.

EXAMPLE 27

(5Z)-(16RS)-2-Decarboxy-1a,1b-dihomo-16,20-dimethyl-5-fluoro-2-formyl-3-oxa-18,18,19,19-tetradehydro-6a-carbaprostaglandin $I_2$ Analogously to Example 25, 610 mg of 2-[(E)-(1S,5S,6R,7R) -7-(tetrahydropyran-2-yloxy)-6-[(3S,4RS)-4-methyl-3-(tetrahydropyran-2-yloxy)non-1-en-6-ynyl]bicyclo [3.3.0]octan-3-ylidene]-2-fluoroethan-1-ol yields 370 mg of the title compound as a colorless oil.

IR: 3610, 3400 (broad), 2963, 2930, 2868, 2731, 1630, 1602, 971 cm$^{-1}$.

EXAMPLE 28

(5Z)-(16RS)-1a,1b-Dihomo16,20-dimethyl-5-fluoro-3-oxa-18,18,19,19-tetradehydro-6a-carbaprostaglandin $I_2$ Analogously to Example 2, 230 mg of the aldehyde produced according to Example 27 yields 125 mg of (5Z)-(16RS)-1a,1b-dihomo -16,20-dimethyl-5-fluoro-3-oxa-18,18,19,19-tetradehydro-6a-carbaprostaglandin $I_2$ 11,15-diacetate. After the blocking groups have been split off, 85 mg of the title compound is obtained as a colorless oil.

IR: 3600, 3410 (broad), 2965, 2930, 2870, 1720, 1602, 970cm$^{-1}$.

EXAMPLE 29

(5Z)-2-Decarboxy-1a,1b-dihomo 5-fluoro-2-formyl-20-methyl-3-oxa-18,18,19,19-tetradehydro16,16-trimethylene-6a-carbaprostaglandin I₂

Analogously to Example 25, 390 mg of 2-[(Z)-(1S,5S,6R,7R)-7-(tetrahydropyran-2-yloxy)-6-[(E)-(3R)-3-tetrahydropyran-2-yloxy)-4,4-trimethylene-non-1-en-6-ynyl]-bicyclo [3.3.0]octan-3-ylidene]-2-fluoroethan-1-ol yields 165 mg of the title compound as a colorless oil.

IR: 3600, 3410 (broad), 2965, 2931, 2870, 2730, 1630, 1601, 970 cm$^{-1}$.

EXAMPLE 30

(5Z)-1a,1b-Dihomo-5-fluoro-20-methyl-3-oxa-18,18,19,19-tetradehydro16,16-trimethylene-6a-carbaprostaglandin I₂

Analogously to Example 2, 190 mg of the aldehyde prepared as described in Example 29 produces 105 mg of (5Z)-1a,1b-dihomo-5-fluoro-20-methyl-3-oxa-18,18,19,19-tetradehydro-16,16-trimethylene-6a-carbaprostaglandin I₂ 11,15-diacetate. After the blocking groups have been split off, 70 mg of the title compound is obtained as a colorless oil.

IR: 3600, 3400 (broad), 2965, 2930, 2870, 1718, 1602, 970 cm$^{-1}$.

EXAMPLE 31

(5Z)-2-Decarboxy-1a,1b-dihomo-16,16-dimethyl-5-fluoro-2-formyl-3-oxa-18,18,19,19-tetradehydro-6a-carbaprostaglandin I₂

In analogy to Example 25, 0.6 g of 2-[(Z)-(1S,5S,6R,7R)-7-(tetrahydropyran-2-yloxy)-6-[(E)-(3R)-4,4-dimethyl-3-(tetrahydropyran-2-yloxy)oct-1-en-6-ynyl]bicyclo [3.3.0]octan-3-ylidene]-2-fluoroethan-1-ol yields 0.27 g of the title compound as a colorless oil.

IR: 3610, 3420 (broad), 2966, 2930, 2868, 2732, 1730, 1602, 971 cm$^{-1}$.

EXAMPLE 32

(5Z)-1a,1b-Dihomo-16,16-dimethyl-5-fluoro-3-oxa-18,18,19,19-tetradehydro-6a-carbaprostaglandin I₂

In analogy to Example 2, 220 mg of the aldehyde obtained according to Example 31 yields 120 mg of (5Z)-1a,1b-dihomo-16,16-dimethyl-5-fluoro-3-oxa-18,18,19,19-tetradehydro-6a-carbaprostaglandin I₂ 11,15-diacetate. After the blocking groups have been split off, 92 mg of the title compound is obtained as a colorless oil.

IR: 3600, 3410 (broad), 2964, 2931, 2870, 1720, 1601, 971 cm$^{-1}$.

EXAMPLE 33

(5Z)-2-Decarboxy-1a,1b-dihomo-5-fluoro-2-formyl-3-oxa-18,18,19,19-tetradehydro16,16,20-trimethyl-6a-carbaprostaglandin I₂

Analogously to Example 25, 0.7 g of 2-[(Z)-(1S,5S,6R,7R)-7-(tetrahydropyran-2-yloxy)-6-[(E)-(3R)-4,4-dimethyl-3-(tetrahydropyran-2-yloxy)non-1-en-6-ynyl]bicyclo [3.3.0]octan-3-ylidene]-2-fluoroethan-1-ol yields 0.38 g of the title compound as a colorless oil.

IR: 3610, 3400 (broad), 2965, 2930, 2870, 2730, 1730, 1601, 970 cm$^{-1}$.

EXAMPLE 34

(5Z)-1a,1b-Dihomo-5-fluoro-3-oxa-18,18,19,19-tetradehydro-16,16,20-trimethyl-6a-carbaprostaglandin I₂

Analogously to Example 2, 0.3 g of the aldehyde prepared according to Example 33 produces 0.16 g of (5Z)-1a,1b-dihomo-5-fluoro-3-oxa-18,18,19,19-tetradehydro-16,16,20-trimethyl-6a-carbaprostaglandin I₂ 11,15-diacetate. After splitting off the blocking groups, 0.12 g of the title compound is obtained as a colorless oil.

IR: 3610, 3400 (broad), 2965, 2868, 1720, 1602, 971 cm$^{-1}$.

EXAMPLE 35

(5Z)-(16RS)-2-Decarboxy-13,14-didehydro-1a,1b-dihomo-5-fluoro-2-formyl16-methyl-3-oxa-18,18,19,19-tetradehydro-6a-carbaprostaglandin I₂

In analogy to Example 25, 0.41 g of 2-[(Z)-(1S,5S,6S,7R)-7-(tetrahydropyran-2-yloxy)-6-[(3S,4RS)-4-methyl-3-(tetrahydropyran-2-yloxy)octa-1,6-diynyl]bicyclo [3.3.0]octan-3-ylidene]-5-fluoroethan-1-ol yields 0.2 g of the title compound as a colorless oil.

IR: 3600, 3410 (broad), 2966, 2731, 2224, 1727 cm$^{-1}$.

EXAMPLE 36

(5Z)-(16RS)-13,14-Didehydro-1a,1b-dihomo-5-fluoro-16-methyl-3-oxa-18,18,19,19-tetradehydro-6a-carbaprostaglandin I₂

In analogy to Example 2, 0.2 g of the aldehyde prepared according to Example 35 yields 0.1 g of (5Z)-(16RS)-13,14-didehydro-1a,1b-dihomo-5-fluoro16-methyl-3-oxa-18,18,19,19-tetradehydro-6a-carbaprostaglandin I₂ 11,15-diacetate. After the blocking groups have been split off, 70 mg of the title compound is obtained as a colorless oil.

IR: 3620, 3400 (broad), 2965, 2870, 2225, 1620 cm$^{-1}$.

EXAMPLE 37

(5Z)-(16RS)-2-Decarboxy-13,14-didehydro-1a,1b-dihomo-16,20-dimethyl-5-fluoro-2-formyl-3-oxa-18,18,19,19-tetradehydro-6a-carbaprostaglandin I₂

In analogy to Example 25, 0.7 g of 2-[(Z)-(1S,5S,6S,7R)-7-(tetrahydropyran-2-yloxy)-6-[(3S,4RS)-4-methyl-3-(tetrahydropyran-2-yloxy)nona-1,6-diynyl]bicyclo [3.3.0]octan-3-ylidene]-2-fluoroethan-1-ol yields 0.38 g of the title compound as a colorless oil.

IR: 3600, 3400 (broad), 2968, 2730, 2225, 1728 cm$^{-1}$.

EXAMPLE 38

(5Z)-(16RS)-13,14-Didehydro-1a,1b-dihomo-16,20-dimethyl-5-fluoro-3-oxa-18,18,19,19-tetradehydro-6a-carbaprostaglandin I₂

Analogously to Example 2, 0.35 g of the aldehyde prepared according to Example 37 yields 0.18 g of (5Z)-(16RS)-13,14-didehydro-1a,1b-dihomo-16,20-dimethyl-5-fluoro-3-oxa-18,18,19,19-tetradehydro-6a-carbaprostaglandin I₂ 11,15diacetate. After the blocking groups have been split off, 0.14 g of the title compound is obtained as a colorless oil.

IR: 3600, 3420 (broad), 2966, 2870, 2226, 1718 cm$^{-1}$.

EXAMPLE 39

(5Z)-2-Decarboxy-13,14-didehydro-1a,1b-dihomo-5-fluoro-2-formyl-20-methyl-3-oxa-18,18,19,19-tetradehydro-16,16-trimethylene-6a-carbaprostaglandin $I_2$ In analogy to Example 25, 1.2 g of 2-[(Z)-(1S,5S,6S,7R) -7-(tetrahydropyran-2-yloxy)-6-[(3S)-3-tetrahydropyran-2-yloxy)-4,4-trimethylene-nona-1,6-diynyl]bicyclo [3.3.0]octan-3-ylidene]-2-fluoroethan-1-ol yields 0.7 g of the title compound as a colorless oil.

IR: 3620, 3420 (broad), 2970, 2731, 2224, 1730 cm$^{-1}$.

EXAMPLE 40

(5Z)-13,14-Didehydro-1a,1b-dihomo-5-fluoro-20-methyl-3-oxa-18,18,19,19-tetradehydro16,16-trimethylene-6a-carbaprostaglandin $I_2$ Analogously to Example 2, 0.6 g of the aldehyde produced according to Example 39 yields 0.31 g of (5Z)-13,14-didehydro-1a,1b -dihomo-5-fluoro-20-methyl-3-oxa-18,18,19,19-tetradehydro-16,16-trimethylene-6a-carbaprostaglandin $I_2$ 11,15-diacetate. After the blocking groups have been split off, 0.25 g of the title compound is obtained as a colorless oil.

IR: 3620, 3425 (broad), 2968, 2870, 2225, 1720 cm$^{-1}$.

EXAMPLE 41

(5Z)-2-Decarboxy-13,14-didehydro-1a,1b-dihomo-16,16-dimethyl-5-fluoro-2-formyl-3-oxa-18,18,19,19-tetradehydro-6a-carbaprostaglandin $I_2$ Analogously to Example 25, 1.4 g of 2-[(Z)-(1S,5S,6S,7R) -7-(tetrahydropyran-2-yloxy)-6-[(3S)-4,4-dimethyl-3-(tetrahydropyran-2-yloxy)octa-1,6-diynyl]-bicyclo [3.3.0]octan-3-ylidene]-2-fluoroethan-1-ol yields 0.65 g of the title compound as a colorless oil IR: 3600, 3420 (broad), 2970, 2930, 2865, 2730, 2225, 1730 cm$^{-1}$.

EXAMPLE 42

(5Z)-13,14-Didehydro-1a,1b-dihomo-16,16-dimethyl-5-fluoro-3-oxa-18,18,19,19-tetradehydro-6a-carbaprostaglandin $I_2$ Analogously to Example 2, 0.4 g of the aldehyde produced according to Example 41 yields 0.22 g of (5Z)-13,14-didehydro-1a,1b-dihomo -16,16-dimethyl-5-fluoro-3-oxa-18,18,19,19-tetradehydro-6a-carbaprostaglandin $I_2$ 11,15diacetate. After the blocking groups have been split off, 0.18 g of the title compound is obtained as a colorless oil.

IR: 3600, 3420 (broad), 2970, 2870, 2224, 1718 cm$^{-1}$.

EXAMPLE 43

(5Z)-2-Decarboxy-13,14-didehydro-1a,1b-dihomo-5-fluoro-2-formyl-3-oxa-18,18,19,19-tetradehydro-16,16,20-trimethyl-6a-carbaprostaglandin $I_2$ Analogously to Example 25, 0.7 g of 2-[(Z)-(1S,5S,6S,7R) -7-(tetrahydropyran-2-yloxy)-6-[(3S)-4,4-dimethyl-3-(tetrahydropyran-2-yloxy)nona-1,6-diynyl]-bicyclo [3.3.0]octan-3-ylidene]-5-fluoroethan-1-ol yields 0.3 g of the title compound as a colorless oil.

IR: 3600, 3420 (broad), 2968, 2932, 2864, 2730, 2225, 1730 cm$^{-1}$.

EXAMPLE 44

(5Z)-13,14-Didehydro-1a,1b-dihomo-5-fluoro-3-oxa-18,18,19,19-tetradehydro-16,16,20-trimethyl-6a-carbaprostaglandin $I_2$ Analogously to Example 2, 0.3 g of the aldehyde produced according to Example 43 yields 0.14 g of (5Z)-13,14-didehydro -1a,1b-dihomo-5-fluoro-3-oxa-18,18,19,19-tetradehydro-16,16,20-trimethyl-6a-carbaprostaglandin $I_2$ 11,15-diacetate. After splitting off the blocking groups, 0.1 g of the title compound is obtained as a colorless oil.

IR: 3605, 3420 (broad), 2970, 2870, 2225, 1720 cm$^{-1}$.

EXAMPLE 45

(5E)-(16RS)-1a,1b-Dihomo16-methyl-3-oxa-18,18,19,19-tetradehydro-6a-carbaprostaglandin $I_2$ Methyl Ester At 0° C., an ethereal diazomethane solution is added dropwise to a solution of 60 mg of (5E)-(16RS)-1a,1b-dihomo-16-methyl-3-oxa-18,18,19,19-tetradehydro-6a-carbaprostaglandin $I_2$ in 10 ml of dichloromethane, until the mixture assumes a permanent yellow coloring. After 5 minutes, the mixture is evaporated under vacuum and the residue chromatographed on silica gel. With ethyl acetate/hexane (4+1), 40 mg of the title compound is obtained as a colorless oil.

IR: 3600, 3400 (broad), 2960, 1740, 974 cm$^{-1}$.

EXAMPLE 46

(5E)-(16RS)-1a,1b-Dihomo16-methyl-3-oxa-18,18,19,19-tetradehydro-6a-carbaprostaglandin $I_2$ Carboxamide A solution is prepared from 105 mg of (5E)-(16RS)-1a,1b-dihomo-16-methyl-3-oxa-18,18,19,19-tetradehydro-6a-carbaprostaglandin $I_2$ in 3 ml of tetrahydrofuran and, at 0° C., combined with 40 mg of triethylamine and 45 mg of isobutyl chloroformate. After one hour, gaseous ammonia is introduced at 0° C. for 10 minutes; then the mixture is allowed to stand for one hour at 24° C. Subsequently the mixture is diluted with 30 ml of water, extracted three times with respectively 30 ml of methylene chloride, the combined organic extracts are shaken with 20 ml of brine, dried over magnesium sulfate, and evaporated under vacuum. After chromatography of the residue on silica gel with methylene chloride/isopropanol (9+1), 78 mg of the title compound is obtained as an oil.

IR: 3610, 3540, 3400 (broad), 2960, 1670, 975 cm$^{-1}$.

EXAMPLE 47

(5Z)-(16RS)-1a,1b-Dihomo-5-fluoro16-methyl-3-oxa-18,18,19,19-tetradehydro-6a-carbaprostaglandin $I_2$ (2,3-Dihydroxypropyl)amide A solution is prepared from 195 mg of (5Z)-(16RS)-1a,1b-dihomo-5-fluoro16-methyl-3-oxa-18,18,19,19-tetradehydro-6a-carbaprostalgandin $I_2$ in 5 ml of acetone and, at 0° C., combined with 60 mg of triethylamine and 75 mg of isobutyl chloroformate. After 20 minutes, a solution of 260 mg of 1-amino-2,3-dihydroxypropane in 8 ml of acetone and 8 ml of acetonitrile is added thereto, and the mixture is stirred for 2 hours at 20° C., then concentrated under vacuum, diluted with methylene chloride, shaken with a small amount of brine, the organic phase is dried with magnesium sulfate, and evaporated under vacuum. After chromatography of the residue on silica gel, methylene chloride/isopropanol (8+2) produces 160 mg of the title compound as a colorless oil.

IR: 3600, 3400 (broad), 2935, 1645, 974 cm$^{-1}$.

EXAMPLE 48

(5Z)-(16RS)-1a,1b-Dihomo-5-fluoro16-methyl-3-oxa-18,18,19,19-tetradehydro-6a-carbaprostaglandin I$_2$ (4-Phenyl)phenacyl Ester A solution is prepared from 120 mg of (5Z)-(16RS)-1a,1b-dihomo-5-fluoro16-methyl-3-oxa-18,18,19,19-tetradehydro-6a-carbaprostaglandin I$_2$ in 3 ml of acetone and combined with 90 mg of ω-bromo-4-phenylacetophenone and 1 ml of triethylamine. The mixture is agitated overnight at room temperature, then combined with 100 ml of ether, shaken twice with respectively 10 ml of water, dried over magnesium sulfate, and evaporated under vacuum. Purification is effected by preparative thin-layer chromatography on silica gel plates developed with ethyl acetate, thus obtaining 128 mg of the title compound.

IR: 3610, 2940, 1740, 1703, 1602, 974 cm$^{-1}$.

EXAMPLE 49

(5E)-(16RS)-1a,1b-Dihomo16-methyl-3-oxa-18,18,19,19-tetradehydro-6a-carbaprostaglandin I$_2$ Tris(hydroxymethyl)aminomethane Salt At 70° C., a solution of 60 mg of tris(hydroxymethyl)aminomethane in 0.2 ml of water is added to a solution of 185 mg of (5E)-(16RS)-1a,1b-dihomo-16-methyl-3-oxa-18,18,19,19-tetradehydro-6a-carbaprostaglandin I$_2$ in 35 ml of acetonitrile. The mixture is allowed to cool under agitation, decanted after 16 hours from the solvent, and the residue is dried under vacuum, thus isolating 160 mg of the title compound as a waxy mass.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A carbacyclin of the formula $$(CH_2)_n-\overset{O}{\overset{\|}{C}}-R_1$$
$$|$$
$$O$$
$$|$$
$$CH_2$$
$$|$$
$$CX$$
$$\|$$

[cyclohexene ring with A—W—D—E—R$_4$ and $\bar{R}_5$ substituents]

wherein
R$_1$ is hydrogen or OR$_2$,
wherein
R$_2$ is (a) hydrogen, (b) C$_{1-10}$ alkyl, (c) C$_{1-10}$ alkyl substituted by halogen; hydroxy; C$_{1-4}$ alkoxy; C$_{6-10}$ aryl; C$_{6-10}$ aryl substituted by 1–3 halogen atoms, a phenyl group, 1–3 C$_{1-4}$ alkyl groups as a chloromethyl, fluoromethyl, trifluoromethyl, carboxy, hydroxy or C$_{1-4}$ alkoxy group; di-C$_{1-4}$-alkylamino; or tri-C$_{1-4}$-alkylammonium; (d) C$_{3-10}$ cycloalkyl, (e) C$_{3-10}$ cycloalkyl substituted by C$_{1-4}$ alkyl, (f) C$_{6-10}$ aryl, (g) C$_{6-10}$ aryl substituted by 1–3 halogen atoms, a phenyl group, 1–3 C$_{1-4}$ alkyl groups or a chloromethyl, fluoromethyl, trifluoromethyl, carboxy, hydroxy or C$_{1-4}$ alkoxy group, (h) an aromatic heterocycle of 5 or 6 ring atoms one of which is O, N or S, the remainder being carbon atoms, or (i)

$$-CH_2-\overset{O}{\overset{\|}{C}}-(C_{6-10}\text{-aryl}),$$

wherein the aryl group is unsubstituted or substituted by (A) (1–3 phenyl groups, each of which is unsubstituted or substituted by 1–3 halogen atoms; (B) 1–3 —C$_{1-4}$-alkoxy groups; or (C) 1–3 halogen atoms;

or R$_1$ is NHR$_3$, wherein R$_3$ is R$_2$ or the acyl group of a C$_{1-15}$-hydrocarbon carboxylic or sulfonic acid;

W is —CHOR—, or $$\begin{array}{c} CH_3 \\ | \\ -C- \\ | \\ OR \end{array}$$

wherein the OR-group is in the α- or β-position;
R is H, tetrahydropyranyl, tetrahydrofuranyl, α-ethoxyethyl, trimethylsilyl, dimethyl-tert-butylsilyl, tribenzylsilyl or an acyl group of a C$_{1-15}$-hydrocarbon carboxylic or sulfonic acid;
n is 3, 4, or 5;
X is hydrogen,
A is —CH$_2$—CH$_2$—, trans—CH=CH—, or —C≡C—, $$\underset{(CH_2)_m}{\overset{\displaystyle -}{\underset{\displaystyle <}{C}}\overset{\displaystyle -}{\underset{\displaystyle >}{C}}CH_2-},$$

C$_{1-10}$-alkylene, or C$_{2-10}$-alkenylene, each of which is optionally substituted by fluorine;
m is 1, 2, or 3;
E is —C≡C—, or —CR$_6$=CR$_7$—, wherein R$_6$ is H, C$_{1-5}$ alkyl and R$_7$ is H, halo or C$_{1-5}$ alkyl;
R$_5$ is OR;
R$_4$ is (a) a C$_{1-10}$ hydrocarbon aliphatic radical, (b) a C$_{1-10}$ hydrocarbon aliphatic radical substituted by C$_{6-10}$ aryl or by C$_{6-10}$ aryl substituted by 1–3 halogen atoms; a phenyl group, 1–3 C$_{1-4}$ alkyl groups or a chloromethyl, fluoromethyl, trifluoromethyl, carboxy, hydroxy or C$_{1-4}$ alkoxy group; (c) C$_{3-10}$ cycloalkyl, (d) C$_{3-10}$ cycloalkyl substituted by C$_{1-4}$ alkyl, (e) C$_{6-10}$ aryl, (f) C$_{6-10}$ aryl substituted by 1–3 halogen atoms, a phenyl group, 1–3 C$_{1-4}$ alkyl groups or a chloromethyl, fluoromethyl, trifluoromethyl, carboxy, hydroxy or C$_{1-4}$ alkoxy group; or (h) an aromatic heterocycle of 5 or 6 ring atoms one of which is O, N or S, the remainder being carbon atoms;

or when $R_1$ is H, a physiologically compatible salt thereof with a base.

2. A compound of claim 1, wherein E is —C≡C—.
3. A compound of claim 1, wherein n is 3.
4. A compound of claim 3, wherein E is —C≡C—.
5. A compound of claim 1 wherein n is 3 and $R_1$ is H or OH.
6. A compound of claim 1, wherein

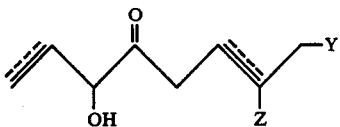

wherein
≡ represents a double or triple bond;
Y is H or $CH_3$;
═ O is H, $CH_3$; $CH_3$, $CH_3$; H, H; or

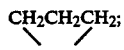

and
Z has no meaning when the adjoining≡group is a triple bond and is H or $CH_3$ when the adjoining═ group is a double bond.

7. (5E)-(16RS)-2-Decarboxy-1a,1b-dihomo-2-formyl-16-methyl-3-oxa-18,18,19,19-tetradehydro-6a-carbaprostaglandin $I_2$, a compound of claim 3.
8. (5E)-(16RS)-1a,1b-Dihomo-16-methyl-3-oxa-18,18,19,19-tetradehydro-6a-carbaprostaglandin $I_2$, a compound of claim 3.
9. (5Z)-(16RS)-2-Decarboxy-1a,1b-dihomo-2-formyl-16-methyl-3-oxa-18,18,19,19-tetradehydro-6a-carbaprostaglandin $I_2$, a compound of claim 3.
10. (5Z)-(16RS)-1a,1b-Dihomo16-methyl-3-oxa-18,18,19,19-tetradehydro-6a-carbaprostaglandin $I_2$, a compound of claim 3.
11. (5E)-(16RS)-2-Decarboxy-1a,1b-dihomo-16,20-dimethyl-2-formyl-3-oxa-18,18,19,19-tetradehydro-6a-carbaprostaglandin $I_2$, a compound of claim 3.
12. (5E)-(16RS)-1a,1b -Dihomo16,20-dimethyl-3-oxa-18,18,19,19-tetradehydro-6a-carbaprostaglandin $I_2$, a compound of claim 3.
13. (5E)-2-Decarboxy-1a,1b-dihomo-2-formyl-20-methyl-3-oxa-16,16-trimethylene18,18,19,19-tetradehydro-6a-carbaprostaglandin $I_2$, a compound of claim 3.
14. (5E)-1a,1b-Dihomo-20-methyl-3-oxa-16,16-trimethylene-18,18,19,19-tetradehydro-6a-carbaprostaglandin $I_2$, a compound of claim 3.
15. (5E)-2-Decarboxy-1a,1b-dihomo-16,16-dimethyl-2-formyl-3-oxa-18,18,19,19-tetradehydro-6a-carbaprostaglandin $I_2$, a compound of claim 3.
16. (5E)-1a,1b-Dihomo16,16-dimethyl-3-oxa-18,18,19,19-tetradehydro-6a-carbaprostaglandin $I_2$, a compound of claim 3.
17. (5E)-2-Decarboxy-1a,1b-dihomo-2-formyl-3-oxa-16,16,20-trimethyl-18,18,19,19-tetradehydro-6a-carbaprostaglandin $I_2$, a compound of claim 3.
18. (5E)-1a,1b-Dihomo-3-oxa-16,16,20-trimethyl-18,18,19,19-tetradehydro-6a-carbaprostaglandin $I_2$, a compound of claim 3.
19. (5E)-(16RS)-2-Decarboxy-18,19-didehydro-1a,1b-dihomo-16,19-dimethyl-2-formyl-3-oxa-6a-carbaprostaglandin $I_2$, a compound of claim 3.

20. (5E)-1a,1b-Dihomo16,19-dimethyl-18,19-didehydro-3-oxa-6a-carbaprostaglandin $I_2$, a compound of claim 3.
21. (5E)-(16RS)-2-Decarboxy-13,14-didehydro-1a,1b-dihomo-2-formyl-16-methyl-3-oxa-18,18,19,19-tetradehydro-6a-carbaprostaglandin $I_2$, a compound of claim 3.
22. (5E)-(16RS)-13,14-Didehydro-1a,1b-dihomo-16-methyl-3-oxa-18,18,19,19-tetradehydro-6a-carbaprostaglandin $I_2$, a compound of claim 3.
23. (5E)-(16RS)-2-Decarboxy-13,14-didehydro-1a,1b-dihomo-16,20-dimethyl-2-formyl-3-oxa-18,18,19,19-tetradehydro-6a-carbaprostaglandin $I_2$, a compound of claim 3.
24. (5E)-(16RS)-13,14-Didehydro-1a,1b-dihomo-16,20-dimethyl-3-oxa-18,18,19,19-tetradehydro-6a-carbaprostaglandin $I_2$, a compound of claim 3.
25. (5E)-2-Decarboxy-13,14-didehydro-1a,1b-dihomo-2-formyl-20-methyl-3-oxa-18,18,19,19-tetradehydro16,16-trimethylene-6a-carbaprostaglandin $I_2$, a compound of claim 3.
26. (5E)-13,14-Didehydro-1a,1b-dihomo-20-methyl-3-oxa-18,18,19,19-tetradehydro16,16-trimethylene-6a-carbaprostaglandin $I_2$, a compound of claim 3.
27. (5E)-2-Decarboxy-13,14-didehydro-1a,1b-dihomo-16,16-dimethyl-2-formyl-3-oxa-18,18,19,19-tetradehydro-6a-carbaprostaglandin $I_2$, a compound of claim 3.
28. (5E)-13,14-Didehydro-1a,1b-dihomo-16,16-dimethyl-3-oxa-18,18,19,19-tetradehydro-6a-carbaprostaglandin $I_2$, a compound of claim 3.
29. (5E)-2-Decarboxy-13,14-didehydro-1a,1b-dihomo-2-formyl-3-oxa-18,18,19,19-tetradehydro-16,16,20-trimethyl-6a-carbaprostaglandin $I_2$, a compound of claim 3.
30. (5E)-13,14-Didehydro-1a,1b-dihomo-3-oxa-18,18,19,19-tetradehydro16,16,20-trimethyl-6a-carbaprostaglandin $I_2$, a compound of claim 3.
31. (5E)-(16RS)-1a,1b-Dihomo-16-methyl-3-oxa-18,18,19,19-tetradehydro-6a-carbaprostaglandin $I_2$ methyl ester, a compound of claim 3.
32. (5E)-(16RS)-1a,1b-Dihomo-16-methyl-3-oxa-18,18,19,19-tetradehydro-6a-carbaprostaglandin $I_2$ carboxamide, a compound of claim 3.
33. (5E)-(16RS)-1a,1b-Dihomo-16-methyl-3-oxa-18,18,19,19-tetradehydro-6a-carbaprostaglandin $I_2$ tris(hydroxymethyl)aminomethane salt, a compound of claim 3.
34. A pharmaceutical composition comprising an amount of a compound of claim 1 effective to lower blood pressure or inhibit thrombocyte aggregation and a pharmaceutically acceptable carrier.
35. A method of lowering blood pressure in a patient in need of such treatment, comprising administering to the patient an amount of a compound of claim 1 effective for such treatment.
36. A compound of claim 24, wherein the 16-methyl group is in the beta-position.
37. A pharmaceutical composition comprising an amount of a compound of claim 36 effective to lower blood pressure or to inhibit thrombocyte aggregation and a pharmaceutically acceptable carrier.
38. A pharmaceutical composition comprising an amount of a compound of claim 24 effective to lower blood pressure or to inhibit thrombocyte aggregation and a pharmaceutically acceptable carrier.
39. A method of lowering blood pressure in a patient in need of such treatment, comprising administering to the patient an amount of a compound of claim 36 effective for such treatment.

40. A method of lowering blood pressure in a patient in need of such treatment, comprising administering to the patient an amount of a compound of claim 24 effective for such treatment.

41. A method of lowering peripheral arterial or coronary vascular resistance in a patient in need of such treatment, comprising administering an effective amount of a compound of claim 1 to the patient.

42. A method of lowering peripheral arterial or coronary vascular resistance in a patient in need of such treatment, comprising administering an effective amount of a compound o claim 24 to the patient.

43. A method of lowering peripheral arterial or coronary vascular resistance in a patient in need of such treatment, comprising administering an effective amount of a compound of claim 36 to the patient.

44. A method of treating peripheral arterial disease or arteriosclerosis in a patient in need of such treatment, comprising administering an effective amount of a compound of claim 1 to the patient.

45. A method of treating peripheral arterial disease or arteriosclerosis in a patient in need of such treatment, comprising administering an effective amount of a compound of claim 24 to the patient.

46. A method of treating peripheral arterial disease or arteriosclerosis in a patient in need of such treatment, comprising administering an effective amount of a compound of claim 36 to the patient.

* * * * *